US00PP35242P2

(12) United States Plant Patent
Koot

(10) Patent No.: US PP35,242 P2
(45) Date of Patent: Jul. 4, 2023

(54) ***LANTANA* PLANT NAMED 'DOLANHEARORA'**

(50) Latin Name: *Lantana camara*
Varietal Denomination: Dolanhearora

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/072,108

(22) Filed: Nov. 30, 2022

(51) Int. Cl.
*A01H 6/86* (2018.01)
*A01H 5/02* (2018.01)

(52) U.S. Cl.
USPC ..... Plt./227

(58) Field of Classification Search
USPC ..... Plt./226, 227
See application file for complete search history.

*Primary Examiner* — Karen M Redden
(74) *Attorney, Agent, or Firm* — C. Anne Whealy

(57) ABSTRACT

A new and distinct cultivar of *Lantana* plant named 'Dolanhearora', characterized by its upright and mounding plant habit; moderately vigorous growth habit and moderate growth rate; freely branching growth habit; dense and bushy plant form; dark green-colored leaves; early and freely flowering habit; long flowering period; flowers that are initially orange in color becoming dark reddish orange with development; and good garden performance.

1 Drawing Sheet

Botanical designation: *Lantana camara.*
Cultivar denomination: 'DOLANHEARORA'.

CROSS-REFERENCED TO CLOSELY-RELATED APPLICATION

Title: *Lantana* Plant Named 'DOLANHAGOL23'
Inventor: Arjan Koot
Filed: Nov. 30, 2022; concurrently with the instant application.

BACKGROUND OF THE INVENTION

The present invention relates to a new and distinct cultivar of *Lantana* plant, botanically known as *Lantana camara* and hereinafter referred to by the name 'Dolanhearora'.

The new *Lantana* plant is a product of a planned breeding program conducted by the Inventor in Rheinberg, Germany. The objective of the breeding program is to create new compact, freely-branching *Lantana* plants with early and freely flowering habit and large attractive flowers.

The new *Lantana* plant originated from a cross-pollination in July, 2019 in Rheinberg, Germany of a proprietary selection of *Lantana camara* identified as code number LA-0124, not patented, as the female, or seed, parent with a proprietary selection of *Lantana camara* identified as code number LA17-000101-001, not patented, as the male, or pollen, parent. The new *Lantana* plant was discovered and selected by the Inventor as a single flowering plant from within the progeny of the stated cross-pollination in a controlled greenhouse environment in Rheinberg, Germany in May, 2022.

Asexual reproduction of the new *Lantana* plant by terminal vegetative cuttings in a controlled greenhouse environment in Rheinberg, Germany since June, 2022 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dolanhearora'. These characteristics in combination distinguish 'Dolanhearora' as a new and distinct *Lantana* plant:

1. Upright and mounding plant habit.
2. Moderately vigorous growth habit and moderate growth rate.
3. Freely branching growth habit; dense and bushy plant form.
4. Dark green-colored leaves.
5. Early and freely flowering habit.
6. Long flowering period.
7. Flowers that are initially orange in color becoming dark reddish orange with development.
8. Good garden performance.

Plants of the new *Lantana* can be compared to plants of the female parent selection. Plants of the new *Lantana* differ primarily from plants of the female parent selection in time to flower as plants of the new *Lantana* flower earlier than plants of the female parent selection. In addition, plants of the new *Lantana* are not as compact as plants of the female parent selection.

Plants of the new *Lantana* can be compared to plants of the male parent selection. Plants of the new *Lantana* differ primarily from plants of the male parent selection in branching habit as plants of the new *Lantana* are more freely branching than plants of the male parent selection. In addition, plants of the new *Lantana* have larger flowers than plants of the male parent selection.

Plants of the new *Lantana* can be compared to plants of the *Lantana camara* 'Dolanhagol 23', disclosed in a U.S. Plant patent application Ser. No. 18/072,088 filed concurrently. In side-by-side comparisons, plants of the new *Lantana* differ from plants of 'Dolanhagol 23' in the following characteristics:

1. Plants of the new *Lantana* are larger and more vigorous than plants of 'Dolanhagol 23'.
2. Plants of the new *Lantana* have larger inflorescences with larger flowers than plants of 'Dolanhagol 23'.
3. Plants of the new *Lantana* and 'Dolanhagol 23' differ in flower color as flowers of plants of the new *Lantana* are initially orange in color becoming dark reddish orange with development whereas flowers of plants of 'Dolanhangol 23' are dark yellow in color.

Plants of the new *Lantana* can also be compared to plants of the *Lantana camara* 'Bant Reda09', disclosed in U.S. Plant Pat. No. 20,531. In side-by-side comparisons, plants of the new *Lantana* differ from plants of 'Bant Reda09' in the following characteristics:

1. Plants of the new *Lantana* are taller and narrower than plants of 'Bant Reda09'.
2. Plants of the new *Lantana* are more vigorous than plants of 'Bant Reda09'.
3. Plants of the new *Lantana* have thicker lateral branches than plants of 'Bant Reda09'.
4. Plants of the new *Lantana* have larger inflorescences than plants of 'Bant Reda09'.
5. Plants of the new *Lantana* and 'Bant Reda09' differ in flower color as flowers of plants of the new *Lantana* are initially orange in color becoming dark reddish orange with development whereas flowers of plants of 'Bant Reda09' are initially orange in color becoming slightly darker orange in color with development.

BRIEF DESCRIPTION OF THE PHOTOGRAPH

The accompanying colored photograph illustrates the overall appearance of the new *Lantana* plant showing the colors as true as it is reasonably possible to obtain in colored reproductions of this type. Colors in the photograph may differ slightly from the color values cited in the detailed botanical description which accurately describe the colors of the new *Lantana* plant.

The photograph is a side perspective view of a typical flowering plant of 'Dolanhearora' grown in a container.

DETAILED BOTANICAL DESCRIPTION

The aforementioned photograph and following observations and measurements describe plants grown during the spring and summer in 13-cm containers in a glass-covered greenhouse in Rheinberg, Germany and under commercial practices typical of commercial *Lantana* production. During the production of the plants, day and night temperatures averaged 18° C. and light levels ranged from 1,500 to 4,500 lux. Plants were pinched three weeks after planting and were twelve weeks old when the photograph was taken and 25 weeks old when the description was taken. In the following description, color references are made to The Royal Horticultural Society Colour Chart, Fifth Edition, except where general terms of ordinary dictionary significance are used. Botanical classification: *Lantana camara* 'Dolanhearora'.

Parentage:

*Female, or seed, parent*.—Proprietary selection of *Lantana camara* identified as code number LA-0124, not patented.

*Male, or pollen, parent*.—Proprietary selection of *Lantana camara* identified as code number LA17-000101-001, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Upright and mounding plant habit; moderately vigorous growth habit and moderate growth rate; freely branching habit, dense and bushy plant form.

*Plant height, soil level to top of foliar plante*.—About 32 cm.

*Plant height, soil level to top of floral plante*.—About 34.3 cm.

*Plant diameter*.—About 56.5 cm.

Lateral branch description:

*Branching habit*.—Freely branching habit with about five primary lateral branches each with about 12 to 14 secondary lateral branches developing per plant.

*Length*.—About 32 cm.

*Diameter*.—About 5.1 mm.

*Internode length*.—About 2.9 cm.

*Strength*.—Strong.

*Texture and luster*.—Pubescent; semi-glossy; longitudinally ridged.

*Color, developing stems*.—Close to 144A.

*Color, developed stems*.—Close to 164B.

Leaf description:

*Arrangement*.—Opposite, simple.

*Length*.—About 6.3 cm.

*Width*.—About 3.7 cm.

*Shape*.—Ovate.

*Apex*.—Acute.

*Base*.—Rounded.

*Margin*.—Senate; sinuses are medium in depth and divergent.

*Texture and luster, upper surface*.—Coarse pubescence; semi-glossy.

*Texture and luster, lower surface*.—Coarse pubescence; matte.

*Venation pattern*.—Pinnate, reticulate.

*Color*.—Developing and fully expanded leaves, upper surface: Close to 137A; venation, close to 144A. Developing and fully expanded leaves, lower surface: Close to 137B; venation, close to 144B.

*Petioles*.—Length: About 1 cm. Diameter: About 1.1 mm. Strength: Moderately strong. Texture and luster:

Smooth, glabrous; matte. Color, upper surface: Close to 144A. Color, lower surface: Close to 144B.

Flower description:

*Flower arrangement and flowering habit*.—Solitary salverform flowers arranged in terminal and axillary hemispherical umbels; flowers face mostly upward or outward depending on their position on the umbel; freely flowering habit with about 32 flowers per inflorescence and numerous inflorescences developing per plant during the flowering season.

*Natural flowering season*.—Early flowering habit, plants begin flowering about eight weeks from unrooted cuttings; long flowering period, plants of the new *Lantana* flower continuously from the spring into the autumn in Germany.

*Flower longevity on the plant*.—Individual flowers last about seven days; flowers persistent.

*Fragrance*.—None detected.

*Inflorescence height*.—About 6.8 cm.

*Inflorescence diameter*.—About 3.8 cm.

*Flower buds*.—Length: About 5.1 mm. Diameter: About 1.8 mm. Shape: Oval to tubular. Texture and luster: Rippled, glabrous; matte. Color: Close to 46A.

*Flowers*.—Appearance: Flared trumpet, salverform; corolla fused, five-parted. Diameter: About 11.1 mm by 9 mm. Depth (height): About 1.6 cm. Throat diameter: About 0.7 mm. Tube length: About 1.2 cm. Tube diameter: About 2 mm.

*Corolla*.—Arrangement: Single whorl of five fused petals. Petal lobe length: About 5 mm. Petal lobe width: About 4 mm. Petal lobe shape: Obovate. Petal lobe apex: Rounded. Petal margin: Entire; slightly undulate. Petal texture and luster, upper and lower surfaces: Smooth, glabrous; matte. Throat texture and luster: Smooth, glabrous; matte. Tube texture and luster: Smooth, glabrous; matte. Color: When opening, upper surface: Close to 24A. When opening, lower surface: Close to 44B. Fully opened, upper surface: Close to 44B; venation, close to 44B; color becoming closer to 44A with subsequent development. Fully opened, lower surface: Close to 44C; venation, close to 44C; color becoming closer to 32C with subsequent development. Throat: Close to 17A; venation, close to 17A. Tube: Close to 43A; venation, close to 43A.

*Calyx*.—Appearance: Tubular calyx with five fused sepals. Sepal length: About 8.5 mm. Sepal diameter: About 1.8 cm. Sepal shape: Ligulate. Sepal apex: Acute. Sepal margin: Entire. Sepal texture and luster, upper surface: Coarse pubescence; semi-glossy. Sepal texture and luster, lower surface: Coarse pubescence; matte. Sepal color, upper surface: Close to 138A. Sepal color, lower surface: Close to 138B.

*Peduncles*.—Length: About 4 cm. Diameter: About 1.1 mm. Strength: Strong. Aspect: Mostly upright. Texture and luster: Pubescent; semi-glossy. Color: Close to 150D.

*Pedicels*.—Length: About 1 mm. Diameter: About 1 mm. Strength: Strong. Aspect: Mostly upright. Texture and luster: Smooth, glabrous; semi-glossy. Color: Close to 145C.

*Reproductive organs*.—Stamens: Quantity and arrangement: Four per flower, adnate to floral tube. Filament length: About 3 mm. Filament color: Close to 158B. Anther length: About 0.8 mm. Anther shape: Oval. Anther color: Close to 17C. Pollen amount: Moderate. Pollen color: Close to 9B. Pistils: Quantity: One per flower. Pistil length: About 4 mm. Style length: About 2.5 mm. Style color: Close to 157C. Stigma diameter: About 0.5 mm. Stigma shape: Round. Stigma color: Close to 144A. Ovary color: Close to N144C. Fruits: Quantity produced per plant: About five during the flowering season. Length: About 5 mm. Diameter: About 7 mm. Texture: Rough. Color: Close to 202A. Seeds: Quantity per flower: About one to five. Length: About 4 mm. Diameter: About 5 mm. Texture: Smooth, glabrous. Color: Close to 200D.

Garden performance: Plants of the new *Lantana* have been observed to have good garden performance and to tolerate wind, rain and to be suitable for USDA Hardiness Zone 11.

Pathogen & pest tolerance: To date, plants of the new *Lantana* have not been observed to be tolerant to pathogens and pests common to *Lantana* plants.

It is claimed:

1. A new and distinct *Lantana* plant named 'Dolanhearora' as illustrated and described.

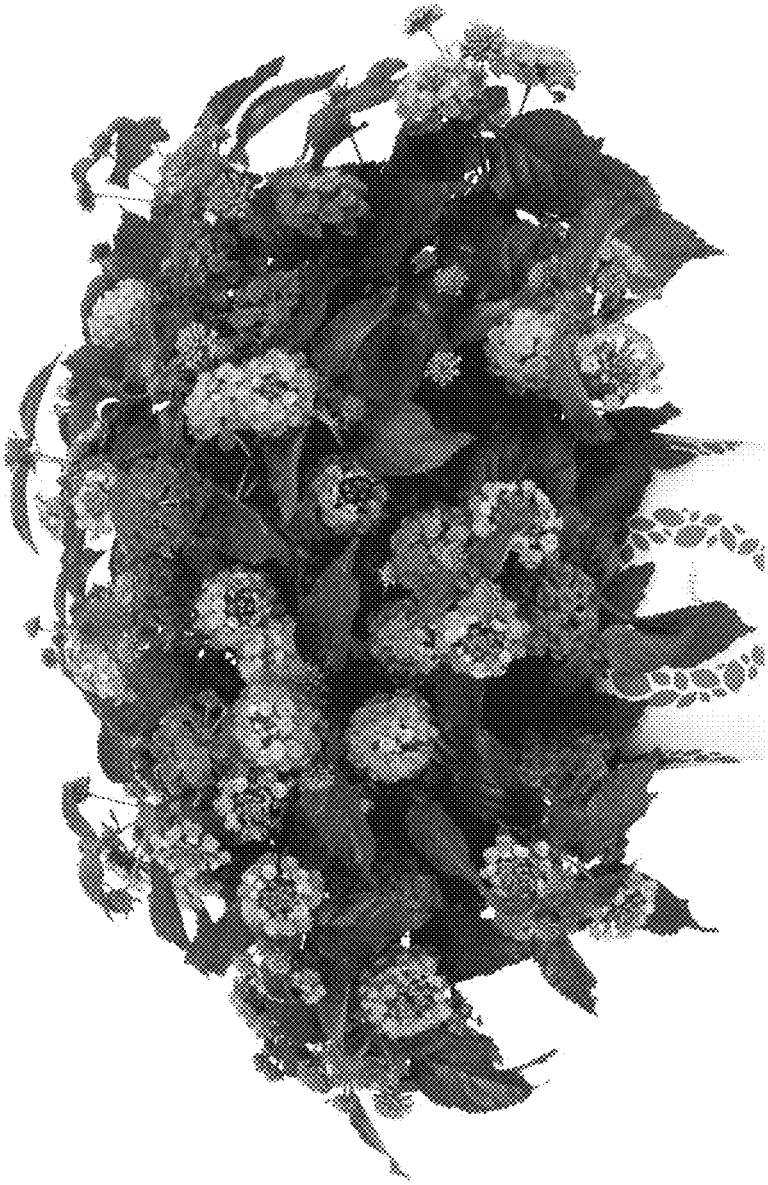

* * * * *